(12) United States Patent
Larter et al.

(10) Patent No.: US 8,495,921 B2
(45) Date of Patent: Jul. 30, 2013

(54) METHOD AND APPARATUS FOR OBTAINING HEAVY OIL SAMPLES FROM A RESERVOIR SAMPLE

(75) Inventors: Stephen Richard Larter, Calgary (CA); Chunqing Jiang, Calgary (CA); Thomas Bernard Paul Oldenburg, Calgary (CA); Jennifer Jane Adams, Houston, TX (US); Kimberley Jane Noke, Calgary (CA); Barry Bennett, Calgary (CA); Ian Donald Gates, Calgary (CA); Lloyd Ross Snowdon, Calgary (CA)

(73) Assignee: Gushor Inc., Calgary, Alberta (CA)

( * ) Notice: Subject to any disclaimer, the term of this patent is extended or adjusted under 35 U.S.C. 154(b) by 654 days.

(21) Appl. No.: 12/526,608

(22) PCT Filed: Feb. 12, 2008

(86) PCT No.: PCT/CA2008/000279
§ 371 (c)(1),
(2), (4) Date: Dec. 17, 2009

(87) PCT Pub. No.: WO2008/098359
PCT Pub. Date: Aug. 21, 2008

(65) Prior Publication Data
US 2010/0089132 A1    Apr. 15, 2010

(30) Foreign Application Priority Data
Feb. 12, 2007 (CA) .................................... 2578319

(51) Int. Cl.
*G01N 1/22* (2006.01)
(52) U.S. Cl.
USPC ..................................................... 73/863.23
(58) Field of Classification Search
None
See application file for complete search history.

(56) References Cited

U.S. PATENT DOCUMENTS

| | | | |
|---|---|---|---|
| 3,491,368 A | * | 1/1970 | Barre et al. ................. 222/642 |
| 4,454,032 A | | 6/1984 | Dupont et al. |
| 4,480,039 A | | 10/1984 | Closmann et al. |

(Continued)

FOREIGN PATENT DOCUMENTS

| | | |
|---|---|---|
| CA | 1330955 | 7/1994 |
| CA | 22622253 | 9/1999 |
| RU | 2101321 | 1/1998 |

OTHER PUBLICATIONS

Office Action mailed Jun. 10, 2011 in related Canadian application No. 2,676,673 (3 pages).

(Continued)

*Primary Examiner* — Peter Macchiarolo
*Assistant Examiner* — Alex Devito
(74) *Attorney, Agent, or Firm* — Fish & Richardson P.C.

(57) ABSTRACT

The invention relates to an apparatus and method to obtain a bitumen or heavy oil sample from an oil reservoir sample, such as a core sample, to enable measurement of physical properties such as viscosity, API gravity, or chemical properties such as sulphur content of the obtained bitumen or heavy oil sample. The analysis performed on the samples obtained in accordance with the invention are effective in assisting oil field operators in making timely drilling and production decisions at the oil reservoir or for routine laboratory extraction of oils and bitumens. The invention also permits the collection of samples from simulated thermal recovery operations and also allows the collection of bitumens and oils for online analysis of live oil physical properties.

33 Claims, 12 Drawing Sheets

U.S. PATENT DOCUMENTS

| | | | |
|---|---|---|---|
| 5,266,196 A | | 11/1993 | Fife et al. |
| 5,394,740 A | * | 3/1995 | Schramm et al. ............ 73/64.48 |
| 5,658,463 A | | 8/1997 | Rubio |
| 5,786,927 A | * | 7/1998 | Greywall ...................... 359/291 |

OTHER PUBLICATIONS

Bhullar, A.G., et al., "Reservoir characterization by a combined micro-extraction—micro-thin layer chromatography (IATROSCAN) method," J. Petroleum Geology (Apr. 2000) vol. 23, No. 2, pp. 221-244.

International Search Report and Written Opinion of the International Searching Authority, PCT Application Serial No. PCT/CA2008/00279, Jun. 4, 2008, 15 pp.

Corrected Version—Written Opinion of the International Searching Authority, PCT Application Serial No. PCT/CA2008/00279, Jun. 20, 2008, 6 pp.

International Preliminary Report on Patentability, International Searching Authority, PCT Application Serial No. PCT/CA2008/00279, Aug. 27, 2009, 15 pp.

First Office Action; Jun. 5, 2012; China; 200880003662.7; 6 pages.

Chinese Patent Office Application No. 200880003662.7, Office action issued Jun. 5, 2012.

* cited by examiner

METHOD AND APPARATUS FOR OBTAINING HEAVY OIL SAMPLES FROM A RESERVOIR SAMPLE

CROSS REFERENCES TO RELATED APPLICATION

This application is a National Stage application under 35 U.S.C. §371 and claims benefit under 35 U.S.C. §119(a) of International Application No. PCT/CA2008/000279, having an International Filing Date of Feb. 12, 2008, which claims the benefit of priority to Canadian Patent Application Serial No. 2,578,319, filed on Feb. 12, 2007, the disclosures of which are incorporated herein by reference in their entirety.

FIELD OF THE INVENTION

The present invention relates generally to an apparatus and method to obtain a bitumen or heavy oil sample from an oil reservoir sample, such as a core or drill cuttings sample.

BACKGROUND OF THE INVENTION

As the world's conventional oil reserves are being consumed, Heavy Oil and Tar Sands (HOTS) reservoirs are becoming increasingly important as a source of petroleum fluids. However, recovery of oil from HOTS reservoirs is generally difficult due to the high viscosity and poor mobility of oil, difficult production and high fluid property heterogeneity in reservoirs. Of the world's petroleum reserves (6 trillion barrels), most exists as heavy oil or oil sand (tar sand) bitumen. Currently, only an average of 17% of this oil can be recovered.

In high porosity and permeability reservoirs, development strategy and production depends on fluid mobility, of which oil viscosity is a major controlling factor. Thus, assessing viscosity of oil throughout HOTS reservoirs is one key to the design and operation of recovery strategies for the production of these high viscosity fluids. This is mostly done by measuring the viscosity of a gas-free bitumen or oil to obtain a dead oil viscosity which can be converted to an in situ live oil viscosity using estimates of bitumen gas content in situ. Ideally, however, the viscosity should be measured directly on a live oil sample that contains the in situ gas content of the reservoir sample, which is mostly not possible due to limitations of the methods by which oil or bitumen is extracted from samples and by which viscosity measured. The large scale fluid property heterogeneity seen across HOTS reservoirs requires detailed fluid property measurement on unaltered oil samples (derived from fresh, "pristine" reservoir samples) and free of mineral fines and water to map viscosity variations in reservoir.

As part of the production appraisal process, it is routine to measure the physical properties (e.g. viscosity, API gravity) and chemical properties such as sulphur content, of the bitumen and heavy oil contained in the reservoirs at closely spaced intervals (every 5 to 10 m or even closer vertically spaced intervals) over the thickness of the reservoir. These analyses must be performed on a water and sediment-free, chemically unaltered representative bitumen or heavy oil sample, which is in the form of liquid petroleum. While analyses can be performed on stored frozen reservoir core samples in the laboratory, ideally these separations of heavy oil or bitumen from reservoir core samples and subsequent viscosity or other measurements should be performed rapidly at the well-site, such that the acquired information from the analyses can be used to assist drilling decisions, particularly with regards to decisions regarding sidetracked wells. For instance, measured oil viscosity may provide useful information to assist in determining if that section of the reservoir is suitable for production.

Presently, techniques of solvent extraction to recover a bitumen sample for viscosity measurement alter the physical properties of heavy oil and tar sand bitumen. Usually, solvents cannot be completely removed without losing some of the low molecular weight petroleum components within the bitumen. Thus, viscosity measurements on solvent extracted bitumen are considered unreliable with existing procedures.

It is possible to mechanically extract heavy oil and tar sand by high speed centrifugation. However, this method proceeds slowly due to the high viscosity of the petroleum in many samples and cannot be performed easily or quickly enough at the well-site. Moreover, even if time is available in a laboratory the expense of engineering-rated centrifuges raises costs dramatically. Furthermore, centrifugation can alter the true composition of the sample by loss of volatile bitumen components, or produce samples of bitumen admixed together with water and fines.

In addition, large quantities of reservoir rock (>0.5 kg or equivalent to a minimum of 30 to 50 cm lengths of slabbed 4" core) are usually required to acquire adequate samples for fluid property determinations, which is both destructive and difficult to handle.

Other methods of recovering very viscous bitumen also include displacement of petroleum with very viscous fluids such as silicone. These techniques are both time-consuming and expensive or ineffective as often insufficient liquid samples are obtained for subsequent physical property testing.

At present, these slow mechanical laboratory petroleum recovery processes are a bottleneck in most bitumen or very heavy oil production planning operations. Thus, there has been a need to provide a rapid and effective recovery method that provides unaltered water and unaltered, sediment free oil or bitumen for viscosity and other analysis, the bitumen or oil retaining its low boiling light end components A review of the prior art indicates that such a system is not known to the inventors.

SUMMARY OF THE INVENTION

The present invention relates generally to an apparatus and method to obtain a sediment and water free oil sample from a bitumen or heavy oil reservoir sample, such as a core sample, or drill cuttings. Formation water samples can also be obtained from heavy oil reservoir samples using the apparatus. The oil sample may then be used to measure physical properties such as viscosity, API gravity, or chemical measurements such as sulphur content of the obtained bitumen or heavy oil sample. The samples collected in accordance with the invention may be rapidly obtained, are of substantially equivalent quality to conventional extraction techniques, and are usually of higher quality in at least some respects. Analyses performed on the samples obtained in accordance with the invention are effective in assisting oil field operators in making timely drilling and production decisions at the oil reservoir or for routine laboratory extraction of oils and bitumens. The invention also permits the collection of samples from simulated thermal or cold recovery operations and also allows the collection of bitumens and oils for online or offline analysis of live oil physical properties.

In one aspect, the invention comprises an apparatus for extracting substantially pure heavy oil or bitumen from a heavy oil or bitumen containing sample, comprising:
  (a) a cylinder and piston assembly for receiving a hydrocarbon-containing sample, the cylinder and piston assembly having a bottom opening;
  (b) means for applying a force to the piston to axially displace the piston within the cylinder;
  (c) a filter assembly disposed across the bottom opening for retaining solid particles within the cylinder, said filter assembly defining openings smaller than about 200 microns;
  (d) fluid collection means associated with the bottom opening.

In one embodiment, the fluid collection means further comprises an atmospheric pressured vial or alternatively a sealed high pressure sampling container capable of taking and maintaining at pressure a gas charged enlivened oil sample.

In one embodiment, the apparatus further comprises fluid connection means disposed below the bottom opening capable of being connected to a capillary viscometer or other pressurized viscometer or other pressurized analytical device to measure viscosity or other properties on the recovered oil, live oil or enlivened oil sample.

In one embodiment, the filter assembly comprises a support member, or is supported by a support member, adapted to withstand a force greater than about 50 MPa and the filter assembly defines openings smaller than about 100 microns. Preferably, the support member is adapted to withstand a force greater than about 100 MPa and the filter assembly defines openings smaller than about 80 microns. More preferably, the filter assembly comprises a porous member having a pore size less than about 20 microns and ideally less than 2 microns.

In one embodiment, the apparatus further comprising means for heating the cylinder or means for cooling the cylinder, or both.

In one embodiment, the apparatus further comprises means for introducing a fluid into the cylinder during sample processing.

In another aspect, the invention comprises a method for extracting fluid heavy oil or bitumen from a reservoir sample, said method comprising the step of mechanically extracting the heavy oil or bitumen through a filter assembly to retain solid particles and allow fluids to pass, by applying sufficient pressure to the sample.

In yet another aspect, the invention comprises a method of simulating a heavy oil recovery process or recovery process preconditioning from an underground reservoir, comprising the steps of:
  (a) placing a sample of the heavy oil reservoir in a mechanical extraction device as described herein;
  (b) adding a recovery agent or a preconditioning agent to be used in the simulated process to the sample;
  (c) allowing a chemical reaction or a physical reaction, or both, to proceed in the device;
  (d) mechanically extracting the heavy oil; and
  (e) measuring relevant properties of the extracted oil.

In another aspect, the invention may comprise a method of simulating a heavy oil recovery process from an underground reservoir, comprising the steps of:
  (a) placing a sample of the heavy oil reservoir in a mechanical extraction device as described herein;
  (b) mechanically extracting the heavy oil at low or high temperatures to simulate a cold or thermal recovery process; and
  (c) measuring relevant properties of the extracted oil

BRIEF DESCRIPTION OF THE DRAWINGS

Embodiments of the present invention are described, by way of example, with reference to the attached Figures, wherein:

(FIG. 5A) and 20° C. (FIG. 5B) for bitumens extracted by the methods of the invention and by centrifugation;

DETAILED DESCRIPTION

Figure 1A:
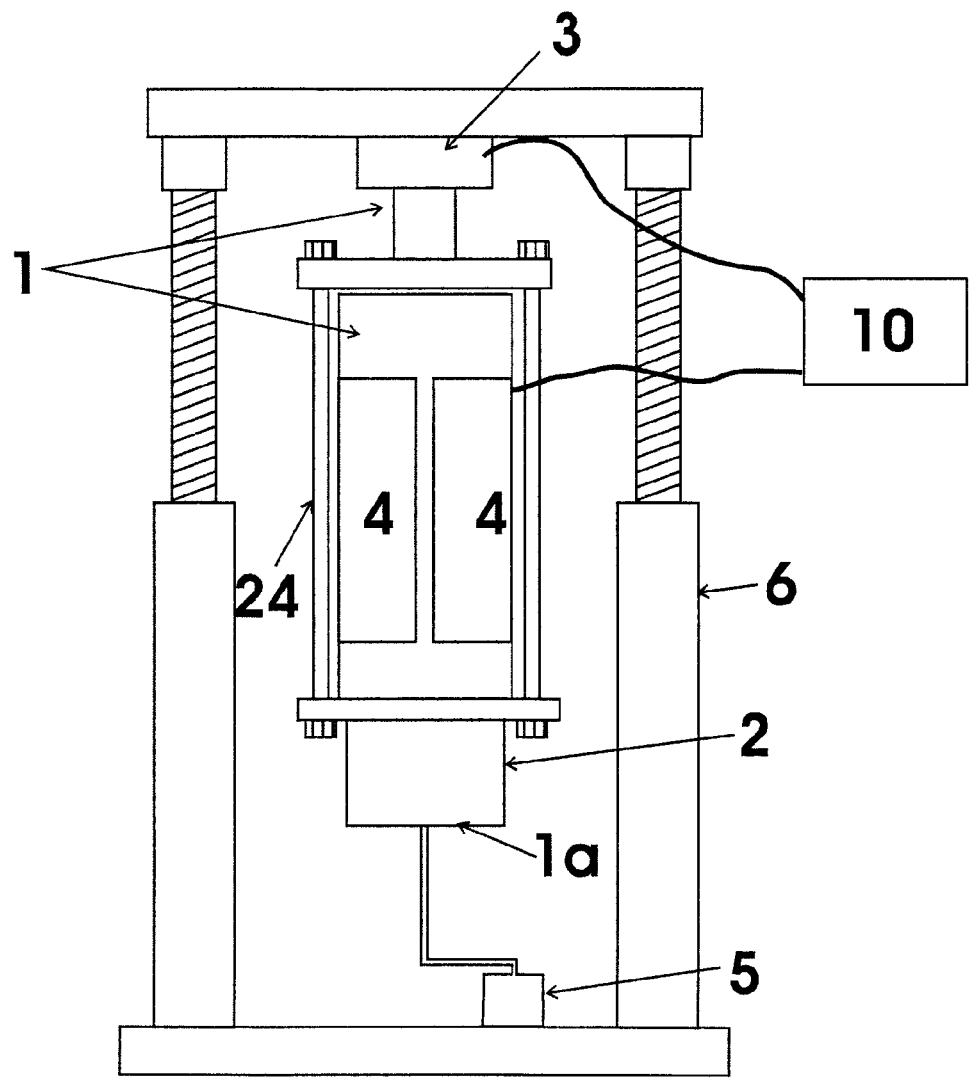
FIG. 1A is a schematic representation of a mechanical displacement device to recover an unaltered bitumen or oil sample for viscosity/API measurement in accordance with the invention.

The present invention relates to a method and apparatus for rapidly obtaining samples of heavy oil or bitumen relatively free of solid fine particles and water from a heavy oil or bitumen reservoir sample, using mechanical force. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

In one embodiment, the apparatus comprises means for obtaining a substantially unaltered bitumen or heavy oil sample from an oil-bearing sample, such as a core sample or drill cuttings, that enable measurement of the physical properties such as viscosity, API gravity, or sulphur content of the obtained bitumen or heavy oil samples. The samples obtained in accordance with the invention are rapidly obtained and are of high quality such that subsequent analyses performed on the samples can provide effective information to assist operators in making timely drilling decisions at the oil reservoir or for helping engineers optimise recovery process designs.

Because the device of the present invention mechanically extracts heavy oil from a sample through a plunging action of a piston in a cylinder, the terms "plunging", "plunger", or "plunged oil" may be used herein to denote the extraction process, the extraction device, or the extracted sample respectively.

One industry accepted definition of heavy oil is petroleum having an API gravity between 22.3° and 10° (920 kilograms/cubic metre to 1,000 kilograms/cubic metre), and extra heavy oil or bitumen as having an API gravity of less than 10° (density higher than 1,000 kilograms/cubic metre). Heavy oil is sometimes defined by a less rigorous definition as oil that is not recoverable in its natural state through a well by ordinary production methods. However, some heavy oil less than 22.3° API does flow very slowly but most requires heat or dilution to flow into a well or through a pipeline. Heavy oil from the Lloydminster area of Alberta and Saskatchewan has API gravities ranging from 9° to 18°. Bitumen is oil that commonly does not flow at ambient conditions, or cannot be pumped without being heated or diluted. Typically, bitumen has viscosities of 10000 cP or higher at 20° C. The bitumen mined from the oilsands deposits in the Athabasca area of Alberta, Canada has an API gravity of around 5-8°.

As used herein, the term "heavy oil" shall mean oil that is less than about 23° API gravity, and includes bitumen associated with oilsands.

Oilsands are mixtures of sand, water, clay and crude bitumen. Each oil sand grain has three layers: an 'envelope' of water surrounding a grain of sand, and a film of bitumen surrounding the water. Heavy oil and bitumen sand reservoirs are often shallowly buried, poorly consolidated sandstones with high porosities (25% or higher) which have been buried to relatively shallow maximum burial depths (less than 3 km, and often less than 1 km).

In apparatus form, one embodiment of the invention comprises a mechanical displacement device, as shown schematically in FIG. 1A. The device generally consists of a cylinder and piston assembly (1) to contain the reservoir sample within the cylinder. The piston mechanically compresses the sample within the cylinder. The cylinder defines a bottom opening (1a). The bottom opening is covered by a basal assembly (2) containing a filter means for retaining the solid portion of a sample, while allowing for efficient transfer of the fluid portions comprising gas, water and oil to flow through. In one embodiment, the filter means comprises a combination of filter elements such as a fine screen mesh, a porous medium disc or a frit. In one embodiment, the basal assembly (2) is pressure sealed against the cylinder by a thermally stable O-ring assembly to provide a complete high pressure seal. The filter means obviously minimizes sand and clay migration through the bottom opening (1a), but allow bitumen and heavy oil to flow into a sample vial or sealable pressure vessel (5) which may be contained within a collection chamber (not shown). The device also includes a press (3) and preferably includes a heating jacket (4) associated with the cylinder. Preferably, the device is mounted in a frame (6) for mechanical stability. The heating element and the press may be operatively connected to a controller (10) which may be manually controlled or automatically controlled by computer program.

The cylinder and piston assembly (1), the filter and the basal assembly (2) must of course be robust enough to withstand the pressure necessary to mechanically extract samples through the filter. In one embodiment, the unit pressure required is above about 50 MPa, and more preferably greater than about 100 MPa. In one embodiment, for most samples, the necessary force may be about 120 MPa (9 tons per square inch of the cylinder cross-sectional area) and may exceed 160-200 MPa (12-15 tons per square inch). In one embodiment, the cylinder comprises a steel cylinder of 8 inches in length, having an inside diameter of 2 inches, and an outside diameter of at least about 2.5 inches, and preferably about 3 inches. Of course, the dimensions may vary depending on the intended sample size, the inherent strength of the material used, and the target pressure to be used.

The piston must be machined to close tolerance to the inside diameter of the cylinder, so as to prevent or minimize leakage between the piston and the cylinder. In a preferred embodiment, it is preferred that the piston have a relatively long skirt which increases piston to cylinder contact area for better sealing, and also improves the stability of the piston within the cylinder. In one preferred embodiment, one or more piston rings (not shown) provide(s) a more complete seal, and may comprise a polymer ring seal, which is inert to chemicals and stable at high temperatures, for example up to 200° C. A seal of this type allows complete retention and recovery of any gas and light end compounds present in the bitumen.

In one embodiment, the filter elements are disposed at the bottom of the cylinder by the basal assembly (2) which fits closely with the bottom of the cylinder. In order to prevent or minimize leakage between the cylinder and the basal assembly (2), it is preferable to have a circular recess within which the cylinder fits, which recess has a diameter which closely matches the outside diameter of the cylinder.

In one embodiment, the filter assembly comprises at least one supporting member, and at least one screening member. The screening member should have small enough openings to retain most solids found in a test sample, while being large enough to permit fluids to pass through relatively unimpeded. The supporting member should be strong enough to withstand the pressing force necessary to mechanically extract the oil. In an alternative embodiment, the basal assembly (2) provides the physical support for the filter assembly, which may be reduced to only the screening member (30).

In one embodiment, the basal assembly (2) is designed to prevent leakage of expelled fluids and to minimize the dead volume of the apparatus to maximise oil recovery. This will prevent the loss of fluid and allow for a better quantitative estimate of the fluids recovered during the extraction process. A sealed base plate (20) with minimized dead volume is also preferred for the collection of reasonably large volumes of pressurized bitumen needed for live oil viscosity measurements where any gas remaining in the bitumen sample in the core is retained. In one embodiment, as shown in FIG. 1C, the seal is provided by an 'O'-ring (22) which seals against the bottom surface of the cylinder, as is shown in FIG. 1D. The cylinder (1) is locked against the base plate (20) by a clamping mechanism (24) such that the 'O'-ring (22) is compressed during the assembly of the basal assembly (2) and cylinder (1) forming a seal (FIG. 1D). As seen in FIG. 1D, the clamping mechanism (24) may comprise a plurality of external bolts which connect members attached to the cylinder (1) and the base plate (20).

The upper surface (26) of the base plate (20) preferably defines a central area which is sized to receive the filter element (30). This central area is surrounded by a ledge (32) which is substantially equal in height to the thickness of the filter element (30), and which forms the sealing surface to the cylinder. Preferably, fluid drainage grooves (34) are formed in the central area, which direct fluids which pass through the filter element (30) into the plunger outlet (1a). In one embodiment, the drainage grooves form a pattern with a plurality of circular and radial grooves, as shown in FIG. 1E. Each groove may be up to 2 mm wide and 2 mm deep. The shape of the bottom of the grooves may be semicircular or square in section.

In one embodiment, the central outlet (1a) comprises a fitting (40) which threads into the bottom of the base plate (20), and which includes, for example, a pressure tight Swagelok™ fitting (42) at the bottom. This fitting (40) allows for pressure vessels, capillary viscometers and other devices to be connected with a pressure tight seal to the plunger outlet.

The fitting (40) could be used to charge the bottom of the assembled plunger apparatus with pressurized fluids or gases prior to plunging and thus can be used to introduce or re-introduce gases or liquids with variable compositions into the core or cuttings sample in the plunger and thereby allow for the recovery of "live" or enlivened oil. As shown in FIG. 1F, a pressurized fluid container (50) may be attached via pipe and valve assembly (8) to the basal assembly fitting (40 & 42).

The filter assembly may be reduced to a single porous metal frit (30) as shown in FIGS. 1C and 1D, or in alternative embodiments, may comprise a plurality of elements of differing thicknesses and opening sizes. For example, the filter assembly may comprises a steel disk which serves as a structural element combined with a mesh cloth, or a porous disk which serves to filter the solids present in the sample.

In general, the filter element defines openings smaller than about 200 microns which are sufficient to allow oil to pass through relatively unimpeded, while retaining a large majority of the solid particles found in a heavy oil or oilsands sample. In a preferred embodiment, the filter may define openings smaller than about 20 microns, and more preferably less than about 15, 10 or even 2 microns to remove clay fraction solid material. In one embodiment, the filter further comprises, as an additional screening member, a mesh wire cloth preferably having a mesh size smaller than about 100 mesh (79 micron nominal opening size), more preferably smaller than about 200 mesh (74 microns). In one embodiment, the wire cloth has a mesh size of about 250 (58 microns).

In one embodiment, the screening member comprises both a mesh wire cloth and a porous metal disk. The porous metal disk may have a pore size of less than about 15 microns, and more preferably less than about 10 microns. If it is desirable to remove extremely fine clay particles, the porous metal disk may have a pore size of about 2 microns, without substantially adversely affecting the operation of the invention.

Manual or computer control of the press (3) increases the normal stress on the sample at a suitable rate, which may be pre-determined by the operator in light of the permeability of the reservoir sample and the compressibility of the sample at the operating temperature of the press. The porosity of the sample is generally not an important factor because the samples are generally loose when loaded. The operating pressure versus time profile that the press follows can be adjusted to deal with the specific observed properties of the sample. Typical compression rates can range up to 10 MPa per minute and are preferably between 1 MPa per minute and 5 MPa per minute.

The device can be various sizes, but typically the piston and cylinder assembly will be sized to hold a reservoir sample of 10 to 1000 cm$^3$, and preferably 100 to 500 cm$^3$. Effluent fluids can be cooled by a cooling jacket (not shown), for example by liquid nitrogen or blown cooled air, if storage of extracted samples or preservation of all lighter fractions is required. Although manual control is effective, the press (3) is preferably automatically controlled by a computer which can apply various compression programs optimized for each sample. In addition, the computer may also be operatively connected to the cylinder heating jacket or the sample cooling jacket, or both, to apply various heating and cooling programs synchronized to the compression programs.

Figure 1B:
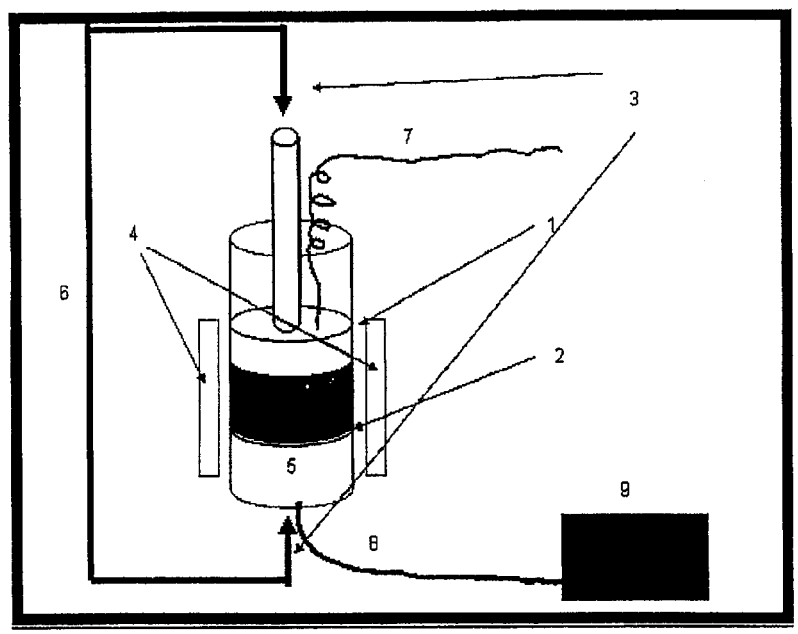
FIG. 1B is a schematic representation of a mechanical displacement device for assessing viscosities during simulation of a recovery process in accordance with one embodiment of the invention.
Figure 1C:
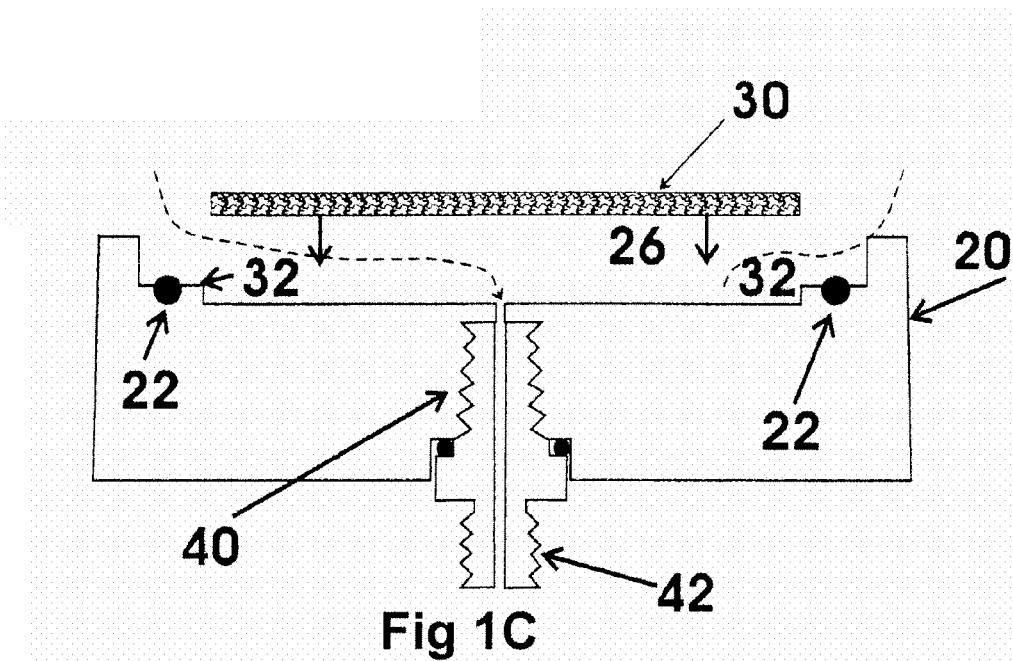
FIG. 1C is a schematic representation of on one embodiment of the basal assembly of the plunger.
Figure 1E:
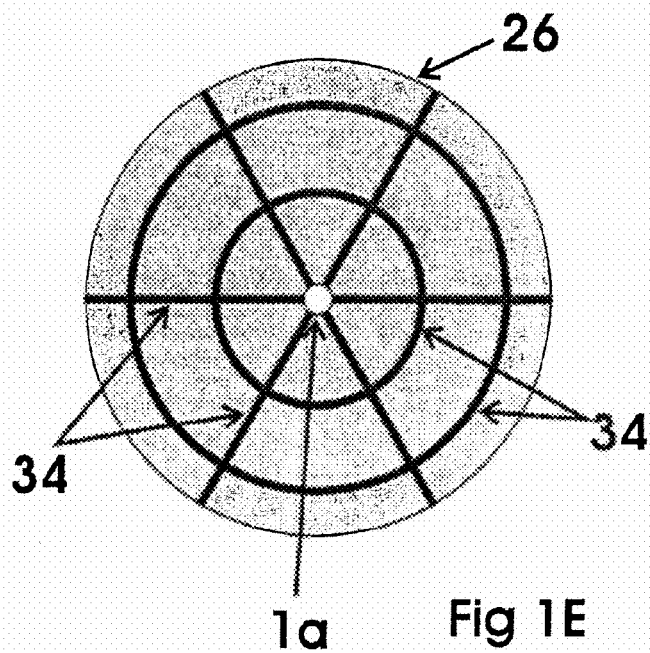
FIG. 1E shows one embodiment of a drainage groove pattern formed by an upper surface of a base plate.
Figure 1D:
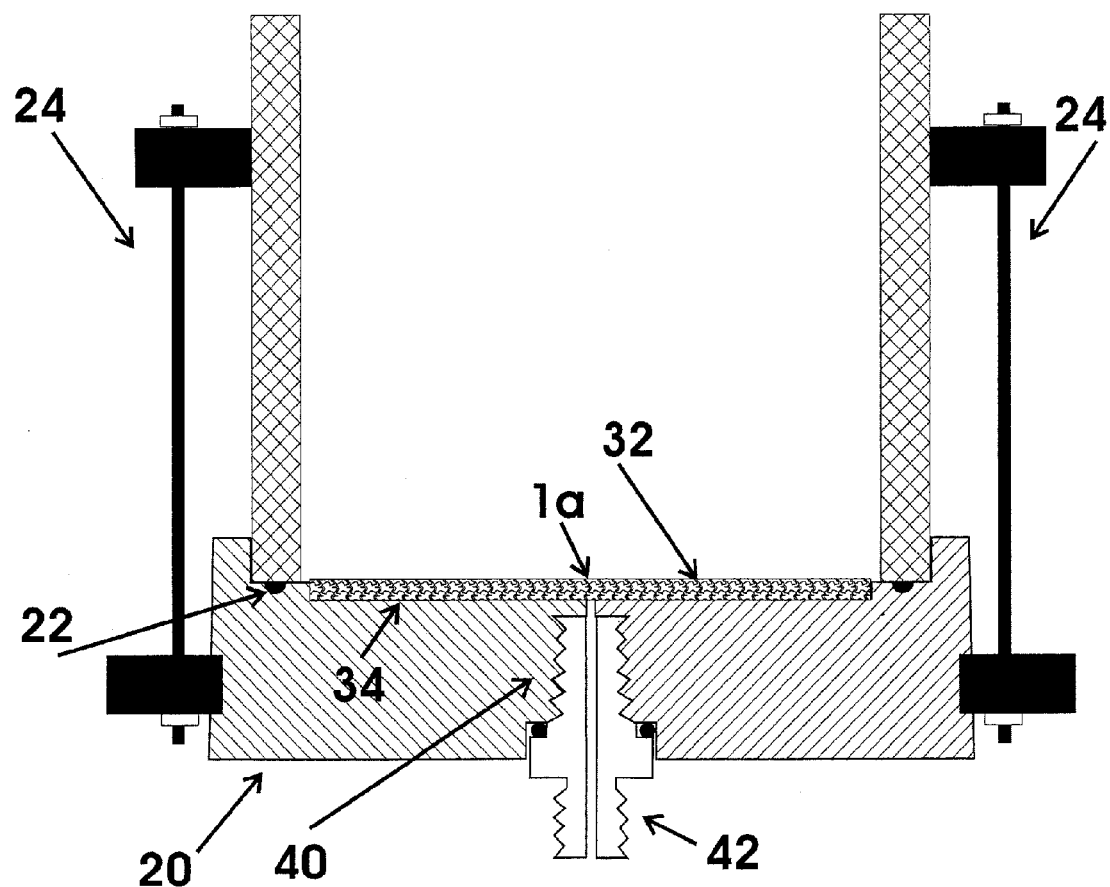
FIG. 1D is a schematic representation of one embodiment of the sealing mechanism between plunger cylinder and basal assembly.
Figure 1F:
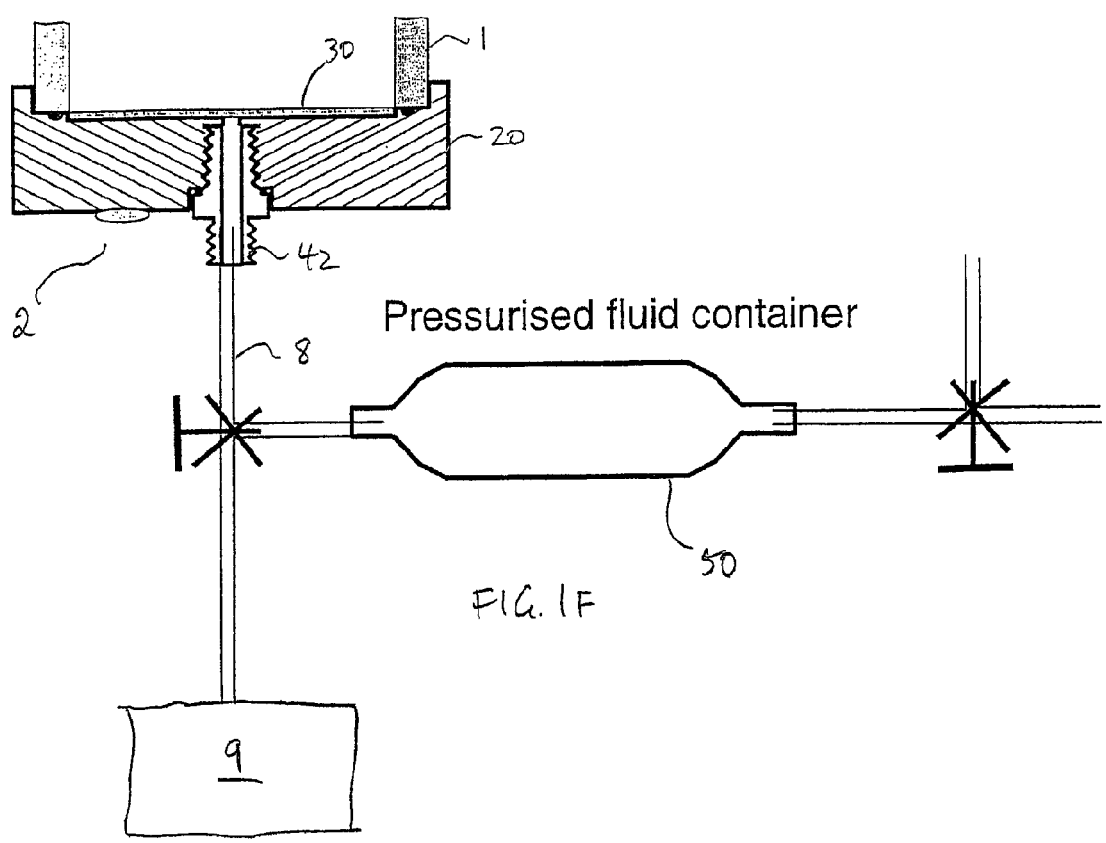
FIG. 1F is a schematic representation of one embodiment showing a pressurized vessel connected to the plunger outlet fitting.

Another embodiment of the device is shown schematically in FIG. 1B. In this embodiment, bitumen or heavy oil fluid properties may be assessed as they evolve during a simulated in situ recovery process where temperature and pressure are varied. This can lead to measurement of properties useful for assessment of the recovery process itself. As shown schematically in FIG. 1B, the device comprises a cylinder and piston assembly (1) which define a plunger cell for containing the reservoir sample, a filter and basal assembly (2), a press (3) and a heating jacket (4). The bitumen or heavy oil sample is collected at the base of the plunger cell (5) via a pipe and valve assembly (8) that can maintain pressure in an analytical device (9) or simply connect to a sample container, which may be sealed and pressurized, for offline PVT analysis. In the analytical device, oil and water are separated, and the oil sample may be analyzed at normal or elevated pressure. The device (9) may include an inline capillary viscometer allowing for direct analysis of the oil for viscosity or other properties at live or dead oil conditions. An injector (7) allows the user to apply a gas or liquid flow under pressure to the top of the sample, before or during bitumen expulsion from the sample. Solution gas may be added to the sample, particularly under pressurized conditions using the injector (7) or via the lower pipe and valve assembly (8). In one embodiment, the addition of solution gas and maintenance of the sample at reservoir conditions of pressure and temperature and gas composition allows for sampling a sample so as to provide accurate analyses of the bitumen or oil samples under "live oil" conditions, mimicking true in situ behavior.

In one example, the application of an additive such as a gas or liquid may be used as a method to precondition the sample. In this method, solids, liquids or gases or combinations of the three with specific preconditioning compositions that may have been introduced into a reservoir can be similarly used to condition the reservoir sample in order to simulate possible recovery processes within the device. In one embodiment, chemical, biological or physical additives can be used to precondition the sample prior to bitumen recovery to simulate an advanced recovery process using those same additives.

The cylinder and piston assembly (1) can also be heated or cooled to simulate phase changes naturally occurring in reservoirs, including gas/liquid/solid conversions, oil or water viscosity modifications, wettability changes and gas/water, hydrate formation or the effect of solvent addition, or combinations thereof.

In one embodiment, the apparatus includes control valves and pressure and temperature gauges (not shown) operatively connected to the device and the control system in order that the vertical load on the sample can be controlled as a function of time. Also, an automated data acquisition system (not shown) can be used to acquire data from the temperature and pressure measurements.

In accordance with a method of the present invention, samples of oil sands core, oil saturated washed reservoir drilling cuttings, bitumen bearing carbonate reservoir samples or other heavy oil bearing samples are mechanically compacted using a mechanical force, such as with hydraulic devices which are capable of producing up to about 200 MPa stress. The force may be equivalent to burial depths of 2 or 3 km or more. The nature or origin of the oil-bearing sample is not intended to be limiting of the claimed invention.

In one embodiment, the force may be applied to the sample at a rate determined by the permeability of the sample or the viscosity of the bitumen, or both. By controlling the compaction rate to promote flow of bitumen or oil separately from any produced water and to prevent extensive grain crushing, substantially sediment and water free bitumen or heavy oil can be expelled from the reservoir. In the case of more viscous bitumen samples, the sample may be subject to mild heat (<100° C.) in the absence of air to aid mobility of the bitumen. The cylinder (1) may be heated by use of a heating jacket (4) or other equivalent means.

Typically, the sample can be uniformly heated to a temperature of 70-80° C. within 5 min by using a thermally-controlled band-heater system. Larger or drier samples may take longer to reach the desired temperature. Heating lowers the viscosity of the bitumen and makes it more mobile under the applied pressure. In one embodiment with sealing devices able to withstand high temperatures, temperatures of up to 350° C. may be applied to simulate a thermal recovery process. For routine application to bitumen recovery for viscosity measurements, heating the bitumen in the sealed airfree environment of the device to 80° C. has been shown to not subsequently alter its measured API gravity or viscosity properties.

Figure 3:
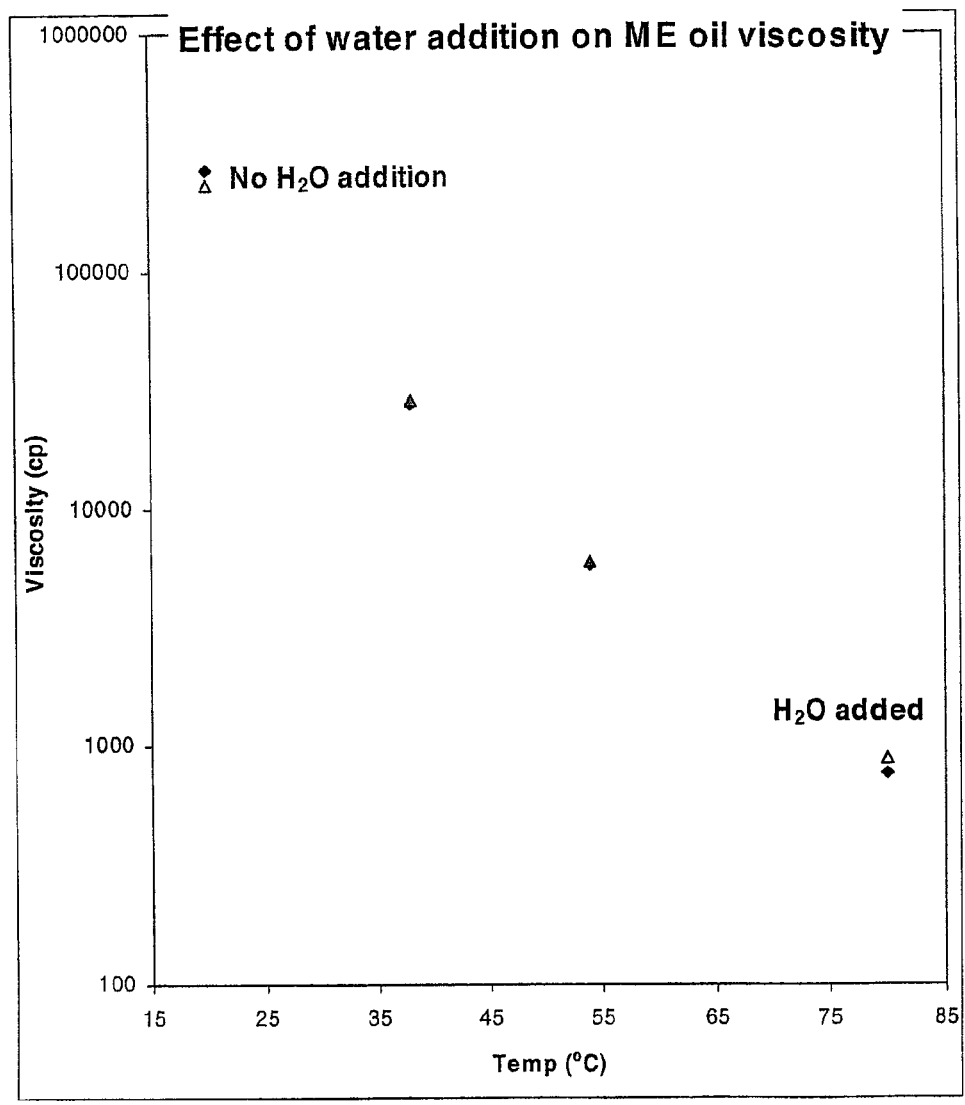
FIG. 3 is a graph showing the effect of water addition to a core sample during bitumen recovery on the viscosity properties of oil recovered with the Mechanical Extraction (ME) technique of this invention (Diamond: No water addition to sample before extraction; open triangle: water added to sample before extraction)

In one embodiment, water may be added to a sample before compaction to aid recovery of heavy oil or bitumen. Added water increases sample conductivity to allow faster sample heating, water increases the fluid saturation in the sample and water also helps transmit pressure to the fluids in the reservoir sample, which aids in fluid displacement. In one embodiment, the added water is typically expelled at lower pressures, therefore, the added water is expelled before the heavy oil fraction flows from the sample. It does not appear that water addition to the reservoir sample has any effect on viscosity of the recovered heavy oil sample (FIG. 3). With a typical oil sands sample, water is expelled at pressures below about 120 MPa, above which oil may begin to be extracted from richer samples. Even without water addition, plunging frozen wet samples typically results in drops of water being extracted before oil begins to be collected. If water is added, the amount of water recovered is at most 80% of the amount added to the sample.

The device expels water before oil or bitumen whether water is added or not. This is because while the relative permeability of water in a reservoir sample from an oil-rich zone of a reservoir can be very low, for example, less than 0.01, the relative difference in viscosity of water and oil at reservoir conditions can be on the order of $10^3$ to $10^6$. The water mobility therefore remains substantially higher than oil mobility in oil-rich zones of heavy oil and bitumen reservoirs. That is, $$kro/\mu ro << krw/\mu rw$$

where:
$kro$ is the relative permeability of the reservoir with respect to oil;
$\mu ro$ is the dynamic viscosity of oil;
$krw$ is the relative permeability of the reservoir with respect to water; and
$\mu rw$ is the dynamic viscosity of water.

The efficiency of water transmission through an oil-rich sample increases as $(krw*\mu o)/(kro*\mu w)$ increases. The mechanical extraction device takes advantage of this mobility contrast to separate the water from the bitumen sample during recovery.

In one embodiment, it has been found that water addition is necessary for samples that have low moisture content, either naturally or as a result of processing or storage. For example, with oilsands which have been crushed and left to dry at ambient conditions for long periods of time (around 10 weeks), substantially no oil can be plunged without water addition. Addition of water also enables the use of spiked tracers, which can enable the chemical and isotopic analysis of any pore waters displaced and mixed with the added water.

The bitumen and heavy oil can be expelled in sufficient quantity such that a typical 200 g core sample from the reservoir can quickly provide, (typically less than 1 hour and often in under 20 minutes), a sufficient quantity of a liquid petroleum (typically up to 5 ml) for API gravity and viscosity measurements as well as chemical analysis. Longer and more forceful extractions may be required for less saturated, low quality, or very viscous samples. For example, carbonate core samples may take approximately 3-4 times longer to extract a similar amount of oil from an oilsands sample, because of the lower permeability of the carbonate core.

Heavy oil can start to appear with as little as 50 MPa of applied pressure for bitumen rich or low viscosity samples. For some cold production type reservoir samples which are both oil rich and have low oil viscosity, oil can flow continuously at a relatively low applied pressure. For more difficult samples that are either very viscous or lean in bitumen or both, little or no bitumen and heavy oil is produced at either low or high pressures. In general, satisfactory oil samples can be obtained from samples with greater than 4.5 wt % bitumen.

By using the mechanical compaction method of the present invention, up to about 50% of the heavy oil or bitumen in a sample may be recovered in a relatively pure state. In general the samples of oil and bitumen obtained are of sufficient quality that the viscosity and API gravity can be measured using commercially available instruments without failures or errors caused by the presence of sediment fines and water Bitumen or heavy oil extracted by mechanical compaction in accordance with the invention as compared to samples obtained by past solvent or centrifuge extraction techniques are very similar chemically and physically. Typically, viscosity or API gravity measurements are broadly similar to those produced from centrifuge recovered bitumens but are lower in viscosity as the mechanical compaction derived oils are enriched in front end compounds such as light hydrocarbons (FIG. 6) and are usually about 1.85 times lower viscosity at 20° C. (FIG. 5B). It should be noted that solvent-extracted oil cannot be used for direct bitumen viscosity measurements.

Importantly, extracted oil derived from the method and apparatus of the invention described herein is recovered rapidly (typically in less than a fifth of the time of centrifuge extracted oils), retaining the low boiling components lost in centrifuge extractions and with minimal costs and may be set up in batches to allow multiple sample extractions in parallel.

The extraction device has the advantage that bitumens or oils can be extracted progressively for physical or chemical testing over a range of production recoveries in a short time whereas centrifugation would necessitate stopping and restarting the separation process. When recovery dependant viscosity or chemical test data are needed, the extraction device provides a method of obtaining effective samples in a controlled manner.

In one embodiment, a method of modeling a physical recovery system may be implemented using an apparatus of the present invention. The apparatus may be heated or cooled to simulate phase changes which naturally occur in reservoirs, including gas-liquid-solid conversions. Various agents such as wettability agents, viscosity modifying agents, or solvents may be introduced during the extraction process to simulate an underground recovery process. These agents are well-known to those skilled in the art and are used to enhance recovery of underground heavy oil formations.

For example, the effectiveness of preconditioning agents in allowing cold production of very viscous heavy oil may be modeled using an embodiment of the present invention, as illustrated in the examples below.

The following examples are provided to illustrate certain aspects of the invention, and are not intended to limit the claimed invention in any manner, unless specifically claimed in that manner.

Example 1

Sample Preparation and Procedure

Bitumen or heavy oil reservoir rocks (containing approximately 5-15 wt % bitumen and having up to 40% porosity) can be mechanically extracted in a single operation. Typically, about 150 to 200 g of lightly disaggregated oil sand sample (oil sand disaggregated while frozen in a mortar and pestle for 5 minutes) is placed in the extraction cylinder (1) to produce between 1 and 10 ml of heavy oil. The amount of sample used depends on the bitumen and heavy oil richness of the sample and the amount of oil required for analysis. For example, a low oil-saturation or low porosity sample would necessitate a larger sample size to ensure that the required liquid oil volume could be extracted.

While water addition to the sample is not necessary with frozen wet core samples, the addition of an amount of water (up to 20 volume percent) to the top of the samples can increase the amount of oil recovered by the procedure, particularly from dried out samples. The water added can be deionised water, tap water, a brine, natural or synthetic formation water, or a tracer spiked water, depending on the application. Samples frozen in freezers are usually thawed for about 15 minutes prior to crushing or for maximum preservation of light ends in a sample can be thawed inside the sealed cylinder. The placement and mechanical extraction operation in the apparatus described here usually takes about 1 hour. The typical steps of the process are described below in a case where water is initially removed from the reservoir sample followed by bitumen or heavy oil extraction:

Example 2

Water Extraction

1. Load an appropriate amount of crushed reservoir sample into the cylinder.
2. Position the piston above the top of the cylinder.
3. Place a water collection vial below within the collection chamber of the ME device.
4. Turn on the heating system to pre-heat (typically 40° C. to 80° C.) the device for approximately 10 minutes.
5. Position the piston at the top of the sample so that it is just in contact with the sample, applying minimal force to the sample. At this point, between about 1 and 10 ml of water will quickly flow into the water collection vial if water has been added to the sample. The piston should be held at this position for several minutes.
6. Increase the load applied by the press to approximately 25 MPa and hold for several minutes. Additional water will flow out if water has been added, otherwise for unwetted native samples only drops of water may be collected.
7. The water sample may be large enough for detailed chemical or isotopic analysis of the water sample.

Example 3

Oil Extraction

The following description relates to an example of one set of conditions that may be applied to extract oil samples from a typical western Canadian tar sand (oil sand) reservoir sample of high porosity.

1. Replace the water collection vial with an oil collection vial that has been weighed.
2. Increase the applied load of the press to about 50 MPa (absolute stress) and hold for 5 minutes. Oil may start dripping into the collection vial at this pressure for rich samples and/or samples containing less viscous oil.
3. Increase the applied load of the press to 75 MPa (absolute stress) and hold for a time interval longer than that in Step 2 (for example, 10 minutes). Increase the applied load of the press to 100 MPa (absolute) and hold for a time interval exceeding that of Step 3 (for example, 15 minutes).
4. Increase the applied load of the press to 25 tons (125 MPa) and hold for a time interval greater than that of Step 4 (for example, 15 minutes).
5. Turn off the heating system and release the press.

The sample collection tube may be weighed to determine the weight of extracted oil, and store the oil in a freezer (if necessary) for subsequent analysis.

The processed reservoir sample may then be unloaded and the apparatus cleaned with solvent or sonication, or both. The apparatus may then be dried in an oven at 70° C. for 10 minutes for the next use.

Older dried out samples may also be processed as follows. With the addition of 30 ml of water to a 150 g oil sand sample which had been crushed and left to dry for 10 weeks in ambient conditions, about 2 ml of oil was produced by the method of the present invention. A frozen sample that was moderately saturated with water was plunged with and without water addition. The results showed that water addition increased the volume of extracted oil significantly (ca. 50%), without any apparent effect on the viscosity of the plunged oil. As shown in FIG. 3, the viscosity of samples extracted with and without water addition at different temperatures is shown to be substantially identical.

Using the 65 minute procedure described above, the amount of bitumen recovered with a single plunging event from 200 g oilsands samples ranged from 2 to 6 g for most samples, which is enough for a dead oil viscosity and API gravity measurement. The actual time window for bitumen collection was usually between 20 to 45 minutes depending on the quality of individual samples. More oil can generally be recovered by leaving the sample under higher pressure and for a longer duration, which may be necessary for more viscous samples containing few volatile components. Data show that up to 50 wt % of bitumen in tar sand samples can be recovered with the plunging technique operated as described above.

Figure 2:
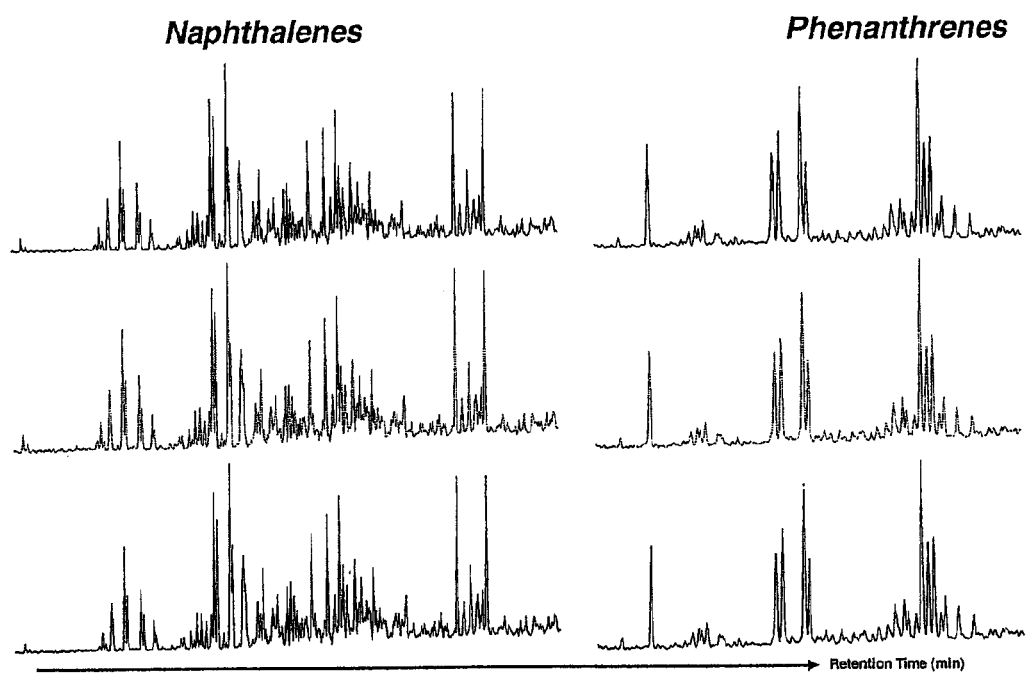
FIG. 2 is a typical analytical trace (a mass chromatogram from gas chromatography-mass spectrometry of an aromatic hydrocarbon fraction) for oils extracted from a reservoir sample by solvent (top), centrifuge (middle) and compaction methodologies (bottom) in accordance with the invention.

The plunging technique described above has been employed for dozens of wells from the tar sands area of northern Alberta to produce bitumen samples for viscosity and API gravity measurements. A comparison of the chemical analysis of a representative but critical fraction (C12+ aromatic hydrocarbon fraction) of bitumen from a Peace River, Northwest Alberta, Canada tar sand sample is shown in FIG. 2. As shown, solvent extracted oils (top trace), spun oils (centrifuge, middle trace) and mechanically extracted oils obtained by the apparatus in accordance with the invention (bottom trace) are very similar for representative alkylnaphthalene and alkylphenanthrene components in the C12+ fraction of a bitumen or heavy oil.

Figure 4:
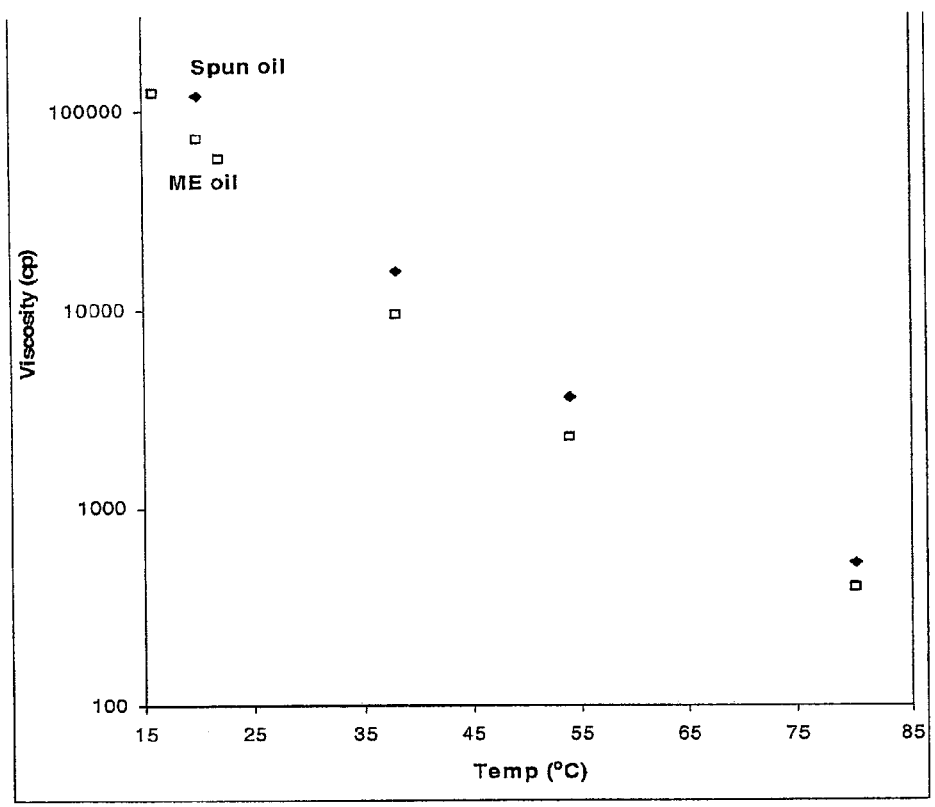
FIG. 4 is a viscosity comparison between ME oil obtained via methods of the invention (open square) and spun oil obtained by a centrifuge technique (solid diamond) in accordance with the prior art.
Figure 6:
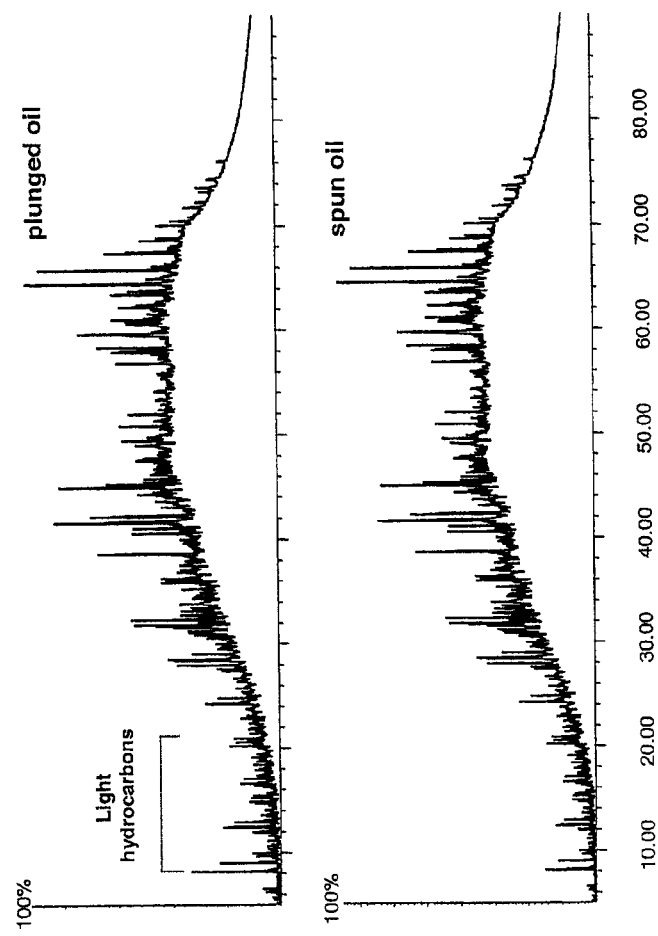
FIG. 6 shows gas chromatograms of bitumens extracted from the same sample by the methods of the invention (plunged oil) and centrifuge (spun oil) showing enrichment in light ends in the plunged sample.

As shown in FIG. 4, the viscosity of oil extracted by plunging and centrifugation shows that plunged oils (open squares) consistently exhibit similar but slightly lower viscosity values than their equivalent spun oils (diamonds) obtained from equivalent samples. At 20° C. plunger recovered bitumens are typically 1.85 times less viscous than centrifuge recovered bitumens due to light end retention. It is believed that these differences are related to the difference in the applied pressures and duration of extraction of the two techniques for recovering bitumen from tar sand samples and the totally sealed nature of the extraction process with the plunger mechanical extraction device. The plunger device consistently recovers bitumens with more retained light hydrocarbon components than equivalent samples extracted with centrifugation (FIG. 6). The currently widely-used spinning technique is a more aggressive method than plunging in that bitumen is extracted at 15000 to 20000 rpm for 1 to 2 hours while the plunger can recover bitumen in much less than 1 hour, often within one half hour. As a result, there is often a higher percentage of volatile and mobile components in plunged oils than in spun oils, making the former less viscous. In addition, the plunged oils from the extraction device may contain a smaller amount of solids (mobile fines) than the spun oil due to retention of fines on the porous disk and screen mesh filters. The physical aspects of the device result in only the mobile oil being exposed to the imposed stress field, while in a centrifuge, the solids (minerals and fines) and fluids experience similar forces and may both be expelled (displaced downwards) simultaneously out from the core material. Additionally as indicated above, the plunger device recovers water before bitumen, so the bitumens obtained are substantially both solid and water free.

Molecular geochemical analyses by gas chromatography-mass spectroscopy show that plunged oils and corresponding spun oils have very similar distributions of geochemical molecular markers, which are consistent with solvent extracted oils, which recovers essentially all of the primary porosity oil (see FIG. 2). This suggests that plunged oils are chemically representative of the reservoired oil and may be most representative of cold produced oils which on average contain less than 5% solids.

Figure 5A:
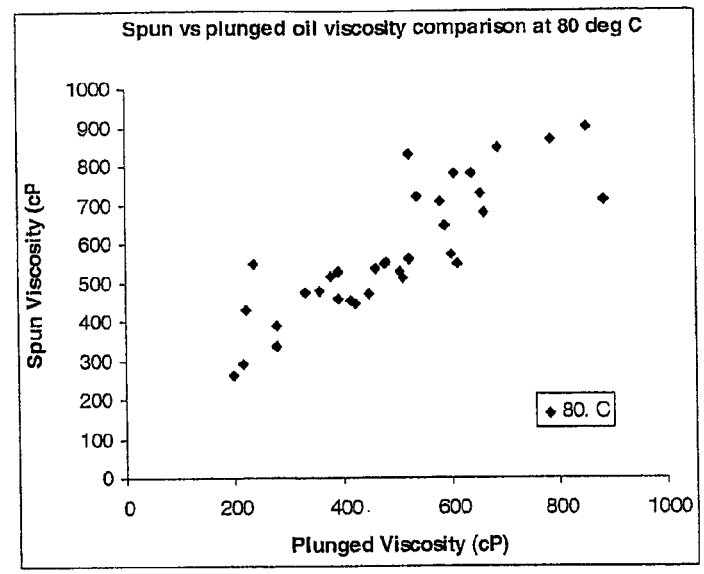
FIGS. 5A and 5B are graphs showing comparable viscosities at 80° C.
Figure 5B:
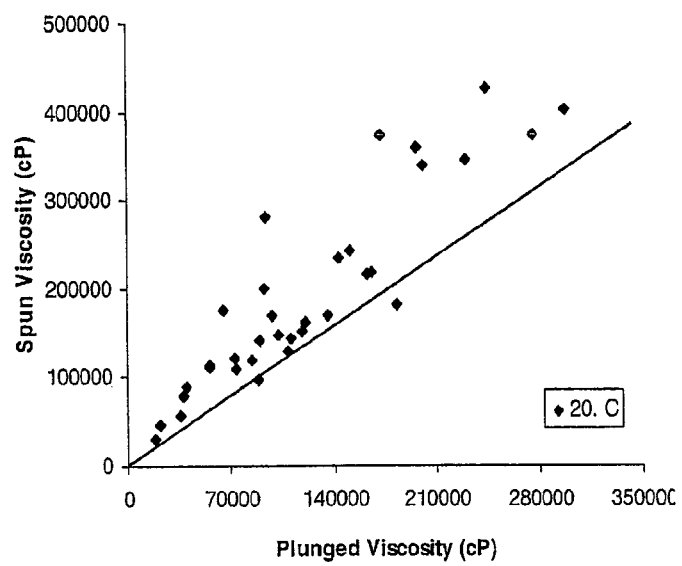
Figure 7:
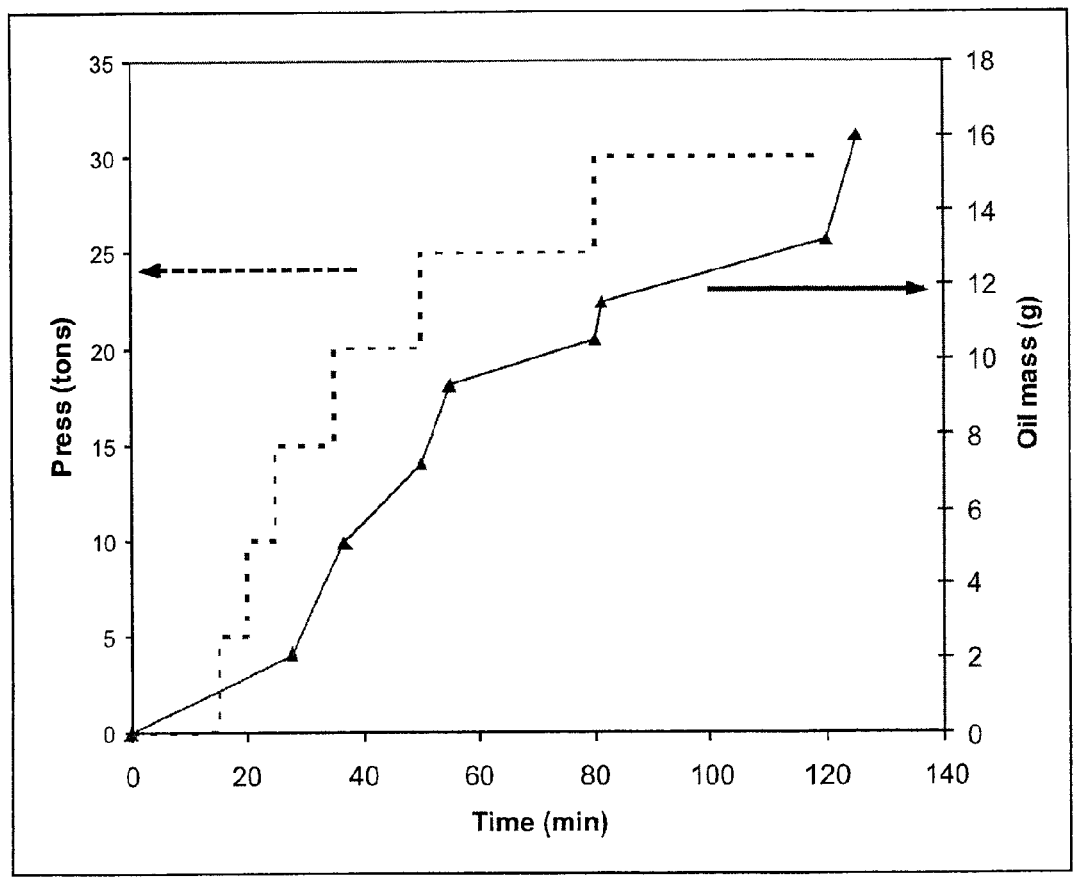
FIG. 7 is a graph showing the effect of a pressure vs. time on extracted mass of bitumen over a range of stress and time; and, FIG. 8 is a graph showing viscosities of a reservoir bitumen sample at 20° C. (solid triangle), 38° C. (open triangle), 54° C. (diamond), 80° C. (star), extracted by the pressure/time profile of FIG. 7.
Figure 8:
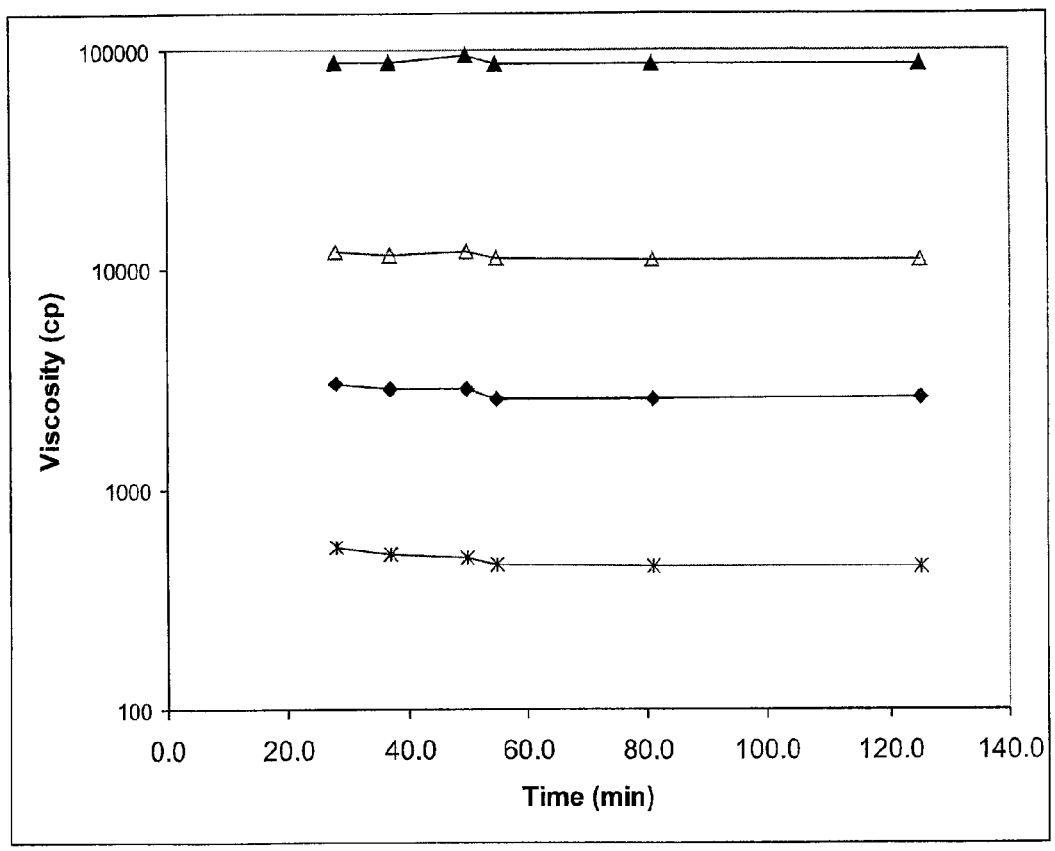

As shown in FIG. 5, the plunged oils show good comparisons of viscosity with equivalent centrifuge recovered or spun oils. Bitumen viscosity at 80° C. and 20° C. measured on bitumens extracted by the plunger and by centrifugation from the same samples are similar but the sealed system plunger retains more bitumen light ends and provides a more realistic in situ bitumen dead oil viscosity measurement typically around 1.85 times lower than the equivalent centrifuge derived bitumens for measurements at 20° C. In FIG. 6, gas chromatograms of the bitumens recovered from the same sample by centrifugation (spun oil) and from mechanical extraction (plunged oil) showing greater retention of light ends (C5-C10) in the plunged oils. Oil viscosity depends exponentially on the proportion of low boiling light end hydrocarbons, so even quite small changes in light end hydrocarbon content can affect viscosity FIGS. 7 and 8 show that bitumen can be recovered gradually over a range of stresses with similar viscosities being evident that are independent of the extent of bitumen recovery from the sample. In FIG. 7, the relationships between the oil mass produced (grams) and the load exerted on the sample (tons) is shown as a function of time. Sufficient oil to measure viscosity can be obtained in half an hour. In FIG. 8, oil viscosity (cP) for bitumens recovered as a function of time from one sample shows little variation with time. Viscosities were measured at, from top to bottom of the diagram, 20, 38, 54, 80° C. Viscosity of early produced oil is very similar to that of late produced oils and valid measurements can be made on most samples from bitumens recovered within one half hour. While most reservoirs show this recovery independent viscosity variation, some reservoirs, especially those oil wet and rich in clay, may show recovery dependent viscosity variations whereby early produced oils are of lower viscosity than later produced oils. This information is very valuable in assessing recovery process possibilities.

Example 4

Use of the Device to Perform a Physical Model Experiment of the Impact of a Preconditioning Agent on an Oil Sands Reservoir Fluids A frozen oil sand core sample with original oil and water distributions in place was placed in the mechanical extraction device and allowed to thaw at room temperature. It was then gently compressed to return the sample to reservoir state, representing a burial depth of about 2 km. Flooding water, including a preconditioning agent, was then flowed slowly over several hours or days through the sample. After an appropriate period of time, bitumen was mechanically extracted from the reservoir sample using the plunging device and was analyzed for viscosity and chemical composition. Table 1 below shows laboratory experimental results achieved when introducing three example preconditioning agents into separate oil sand samples. One agent, phenol, changes the sample wettability allowing oil to stick to mineral grains, while two water soluble organic solvents (MPK and MTBE) partition into oil in the core sample and reduce its viscosity. During the experiment, aliquots of 225 grams of the oil sand sample were compacted to reservoir conditions. A water solution in the amount of 20 ml, which represented approximately a volume of water equal to three times the volume of water in the samples residual water film (i.e., three pore film volumes) and including the example preconditioning agents at saturation solubility in water were added on top of the sample in the mechanical extraction device. The water solution was gently flooded through the oil sand sample pore system using a pressure gradient provided by slow compression of the fluid and sample, after which the contents were left standing for approximately three hours at ambient temperature. The device was then operated to simulate a recovery process by applying a pressure gradient to the sample as described above in Example 3 to recover fluid samples from the device. Oil and water was collected from the simulated recovery process and viscosities and chemical compositions thereof were measured.

TABLE 1

| Water solution composition | Load at which oil flow starting | Oil amount recovered | Viscosity (cP) 20° C. | 50° C. | 80° C. |
|---|---|---|---|---|---|
| 20 ml H$_2$O saturated w. MPK | 8-10 tons | 12.4 g | 18951 | 1461 | 288 |
| 20 ml H$_2$O saturated w. MTBE | 8 tons | 10.9 g | 50470 | 2498 | 401 |
| 20 ml H$_2$O saturated w. Phenol | 12-14 tons | 9.9 g | 64691 | 2600 | 351 |
| 20 ml H$_2$O w/o additives | 12-14 tons | 7.3 g | 182069 | 5391 | 557 |

The second column in Table 1 indicates the load on the sample at which oil began to flow during the recovery process which was carried out at 85° C. The third column indicates the amount of oil recovered. The fourth, fifth and sixth columns show the viscosity of the recovered oil measured at temperatures of 20, 50 and 80° C. respectively. The first row shows the results when the preconditioning agent was an aqueous solution of methyl propyl ketone (MPK), which modifies oil viscosity. The second row shows the results when the preconditioning agent was an aqueous solution of methyl tertiary-butyl ether (MTBE), which also modifies oil viscosity. The third row shows the results when the preconditioning agent was an aqueous solution of phenol, a preconditioning agent which affects the wettability of the sample to promote retention of polar compounds in the rock sample during recovery and thus decrease viscosity. The fourth row shows, for comparative purposes, the results when the oil sand sample is left untreated.

As is illustrated by the above experimental results, the amount of oil recovered increased significantly after preconditioning with the phenol, MPK or MTBE preconditioning agent. The reason for the increased recovery can be attributed, at least in part, to the effect on viscosity by the preconditioning process involving either solvent partition into the oil from the water (MTBE, MPK) and wettability change and solvent partition (phenol). The viscosity was reduced significantly relative to the control sample, particularly at the lower temperatures. Cold production of a heavy oil or bitumen reservoir can occur if the viscosity of the dead oil is less than approximately 50,000 cP at 20° Celsius. By using either the phenol or MPK or MTBE as a preconditioning agent, oil otherwise unrecoverable by cold production due to a high viscosity (180,000 cP at 20° Celsius) can be produced by cold production if its viscosity after preconditioning is below the threshold required for cold production. In this example non cold production petroleum was converted by preconditioning into cold production petroleum using MTBE or MPK or phenol prefloods.

The plunger device thus can be used to quickly test reservoir preconditioning agents in this manner and can also be used to simulate cold and thermal recovery of bitumen from a reservoir sample, with or without the use of preconditioning agents.

As live oil samples can be collected and even be characterized on line for viscosity with the device, the plunger represents a very cost effective and rapid means of screening many possible combinations of reservoir preconditioning and recovery process methods in addition to providing high quality water and sediment free bitumens for viscosity and API gravity analysis.

The invention claimed is:

1. An apparatus for extracting substantially pure heavy oil or bitumen from a core sample comprising a heavy oil or bitumen, comprising:
   (a) a cylinder and piston assembly that receives the core sample, the cylinder and piston assembly having a bottom opening;
   (b) means for applying a force to the piston to axially displace the piston within the cylinder and press the sample against a filter assembly, where the force is applied at a rate determined by a relationship between a mobility of the heavy oil or bitumen contained in the sample and a mobility of an aqueous fluid contained in the sample;
   (c) the filter assembly disposed across the bottom opening for retaining solid particles within the cylinder, said filter assembly defining openings smaller than about 200 microns; and
   (d) fluid collection means disposed below the bottom opening of the cylinder and including a base plate pressure sealed against a surface of the cylinder and where the filter assembly is mounted in the base plate.

2. The apparatus of claim 1, wherein the base plate includes a plurality of fluid collection grooves connecting to a central opening, and having a minimal dead volume.

3. The apparatus of claim 2, wherein the filter assembly comprises a support member adapted to withstand a force greater than about 50 MPa and the filter assembly defines openings smaller than about 100 microns.

4. The apparatus of claim 3, wherein the support member is adapted to withstand a force greater than about 100 MPa and the filter assembly defines openings smaller than about 80 microns.

5. The apparatus of claim 4, wherein the filter assembly comprises a porous member having a pore size less than about 20 microns.

6. The apparatus of claim 2, wherein the fluid collection means further comprises a fitting which permits gas-tight connection to a fluid collection container.

7. The apparatus of claim 6, wherein the fitting further comprises a gas-tight connection to a fluid source for injection into the cylinder.

8. The apparatus of claim 1, further comprising means for heating the cylinder.

9. The apparatus of claim 1, further comprising means for cooling the fluid collection means.

10. The apparatus of claim 1, further comprising means for introducing a fluid into the cylinder before or during sample processing.

11. The apparatus of claim 1, further comprising means for measuring viscosity of heavy oil or bitumen collected from the sample, operatively connected to the fluid collection means.

12. A method for extracting fluid heavy oil or bitumen from a reservoir core sample, said method comprising:
   introducing the reservoir core sample into a cylinder and piston assembly including a filter assembly positioned at an end of the cylinder;
   determining a force to apply against the piston based on a relationship between a mobility of the heavy oil or bitumen contained in the core sample and a mobility of an aqueous fluid contained in the core sample; and
   exerting the determined force against the piston to press the core sample against the filter assembly and mechanically extract the heavy oil or bitumen from the core sample, where solid particles of the core sample are retained in the cylinder and fluids are allowed to pass through;
   wherein the force is determined such the heavy oil or bitumen extracted from the core sample retains low boiling point components and is substantially free of the aqueous fluid.

13. The method of claim 12, wherein the determined force is such that the aqueous fluid is separately extracted before the heavy oil or bitumen is extracted.

14. The method of claim 13, further comprising analyzing the extracted aqueous fluid.

15. The method of claim 12, further comprising heating the core sample to above about 30° C.

16. The method of claim 15, wherein the core sample is heated above about 50° C.

17. The method of claim 12, further comprising enclosing the core sample in a gas-tight chamber and introducing an additive to the chamber before or during mechanical extraction of fluid from the core sample.

18. The method of claim 17, wherein the additive is chosen to simulate reservoir conditions.

19. The method of claim 18, wherein the additive comprises solution gas.

20. The method of claim 12, further comprising cooling the collected fluid extracted from the core sample.

21. The method of claim 12, further comprising mixing water with the core sample prior to mechanical extraction.

22. The method of claim 12, further comprising pressurizing the collected fluid extracted from the core sample with or without solution gas.

23. The method of claim 12, further comprising measuring a property of the collected fluid.

24. The method of claim 12, further comprising repeatedly pressurizing the core sample by cyclic loading of the piston.

25. A method of simulating a heavy oil or bitumen recovery process or recovery process preconditioning from an underground reservoir, comprising the steps of:
   (a) placing a core sample of the underground reservoir in a cylinder and piston assembly;
   (b) adding a recovery agent or a preconditioning agent to be used in the simulated process to the core sample;
   (c) allowing a chemical reaction or physical reaction, or both, to proceed in the cylinder and piston assembly;
   (d) applying a force to the piston to press the core sample against a filter assembly positioned at an end of the cylinder and mechanically extracting the heavy oil or bitumen from the sample, the force determined by a relationship between a mobility of the heavy oil or bitumen contained in the core sample and a mobility of an aqueous fluid contained in the core sample; and
   (e) measuring relevant properties of extracted fluid.

26. The method of claim 25, wherein the recovery agent is added as an aqueous solution or emulsion, the method further comprising extracting an aqueous portion before extracting the heavy oil or bitumen.

27. A method of simulating a heavy oil recovery process from an underground reservoir, comprising:
   (a) placing a core sample of the underground reservoir in a cylinder and piston assembly;
   (b) applying a force to the piston to press the core sample against a filter assembly positioned at an end of the cylinder and mechanically extracting the heavy oil at low or high temperatures to simulate a cold or thermal recovery process, the force determined by a difference between a mobility of water contained in the sample and a mobility of the heavy oil contained in the sample;
   (c) measuring relevant properties of the extracted oil;
   (d) extracting at least a portion of the water in the core sample; and
   (e) separately from the water, extracting the heavy oil from the core sample, the extracted heavy oil being substantially free from a plurality of solid particles of the sample.

28. The method of claim 27, further comprising repeatedly pressurizing the core sample by cyclic loading of the piston.

29. A method for extracting fluid water from a reservoir core sample, said method comprising:
   introducing the core sample into a cylinder and piston assembly including a filter assembly positioned at an end of the cylinder;
   determining a force to apply against the piston based on a difference between a mobility of water contained in the core sample and a mobility of the heavy oil or bitumen contained in the core sample, such that the heavy oil or bitumen is extracted from the core sample separately from the water in the sample and separately from a plurality of solid particles of the core sample;
   exerting the determined force against the piston;
   pressing the core sample against the filter assembly with the piston; and
   mechanically extracting the water from the core sample, where solid particles are retained in the cylinder and fluids are allowed to pass through,
   wherein the force is determined such the water extracted from the core sample is substantially free of solid particles and the heavy oil or bitumen.

30. The apparatus of claim 1, wherein the mobility of the heavy oil or bitumen is determined based on experimental data.

31. The apparatus of claim 1, wherein the force is determined such that the heavy oil or bitumen is extracted from the core sample separately from the aqueous fluid in the core sample and separately from a plurality of solid particles of the core sample.

32. The method of claim 12, wherein the mobility of the heavy oil or bitumen is determined based on experimental data.

33. The method of claim 12, wherein exerting the determined force against the piston to press the core sample against the filter assembly and mechanically extract the heavy oil or bitumen from the sample comprises:
   extracting the heavy oil or bitumen from the core sample separately from the aqueous fluid in the core sample and separately from a plurality of solid particles of the core sample.

* * * * *